United States Patent [19]

Mizuno et al.

[11] Patent Number: 5,498,721
[45] Date of Patent: Mar. 12, 1996

[54] PROCESS FOR PRODUCING THIOPHENE DERIVATIVES

[75] Inventors: Masahiko Mizuno, Ibaraki; Isao Kurimoto, Oita; Norihiko Hirata, Suita; Toshiya Takahashi, Ibaraki; Masayoshi Minai, Moriyama; Takahiro Yamamoto, Oita; Tadashi Mizuno, Ibaraki; Yasunobu Miyamoto, Takatsuki, all of Japan

[73] Assignee: Sumitomo Chemical Company, Limited, Osaka, Japan

[21] Appl. No.: 271,657

[22] Filed: Jul. 7, 1994

[30] Foreign Application Priority Data

| Jul. 8, 1993 | [JP] | Japan | 5-168985 |
| Jul. 12, 1993 | [JP] | Japan | 5-171490 |
| Jul. 14, 1993 | [JP] | Japan | 5-174440 |
| Dec. 27, 1993 | [JP] | Japan | 5-333797 |

[51] Int. Cl.$^6$ ............................................. C07D 495/04
[52] U.S. Cl. ................................................ 548/303.7
[58] Field of Search .................................... 548/303.7

[56] References Cited

U.S. PATENT DOCUMENTS

| 4,130,712 | 12/1978 | Vasilevskis. | |
| 4,189,586 | 2/1980 | Baggiolini et al. | 548/303.7 |
| 4,247,704 | 1/1981 | Baggiolini et al. | 548/303.7 |
| 4,284,557 | 8/1981 | Baggiolini et al. | |

FOREIGN PATENT DOCUMENTS

| 0019788 | 12/1980 | European Pat. Off.. |
| 0084377 | 7/1983 | European Pat. Off.. |
| 2358407 | 2/1978 | France. |
| 49-15277 | 4/1974 | Japan. |
| 53-27279 | 8/1978 | Japan. |
| 61-151194 | 7/1986 | Japan. |
| 63-8954 | 2/1988 | Japan. |

OTHER PUBLICATIONS

Johnstone, Robert A. W. and Wilby, Anna H. Chem. Rev. 1985 85, 129–170.
Tour, James M.; Copper, Joel P. and Pendalwar, Shekhar L. J. Org. Chem. 1990, 55, 3452–3453.
Stern, E. W.; Maples, P. K. J. Catal. 1972, 27 (1) 120–133.
Chemical Abstracts, vol. 81, No. 23, 1974(5) 15223k.

*Primary Examiner*—Robert W. Ramsuer
*Assistant Examiner*—Laura L. Stockton
*Attorney, Agent, or Firm*—Cushman Darby & Cushman

[57] ABSTRACT

A process for producing a thiophene derivative represented by a general formula (2) involves catalytically reducing a compound represnted by the general formula (1) with hydrogen in a solvent mixture of at least one of alcohol and water in the presence of a palladium catalyst soluble in organic solvents. A thiophene derivative is useful in preparing biotin (Vitamin H).

24 Claims, No Drawings

PROCESS FOR PRODUCING THIOPHENE DERIVATIVES

BACKGROUND OF THE INVENTION

1. Field of the Invention

The present invention relates to a process for producing a thiophene derivative. More particularly, the present invention relates to a process for producing a thiophene derivative useful for an intermediate of biotin (vitamin H).

2. Description of the Related Art

There has been known heretofore a process for producing a thiophene as expressed by the general formula (2):

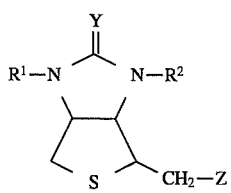

as disclosed in Japanese Patent KOKAI (Laid-open) No. Sho 61-151194. This process uses palladium oxide as a palladium catalyst.

However, the above process has a disadvantage of requiring a great amount of the expensive palladium catalyst for the production of the compounds expressed by the general formula (2) owing to a low catalytic activity in the process.

SUMMARY OF THE INVENTION

An object of the present invention is to provide a process for producing a thiophene derivative (2) advantageous in industry in that the amount of the expensive palladium catalyst to be used can be reduced to a great extent.

That is, the present invention provides a process for producing a thiophene derivative expressed by the general formula (2):

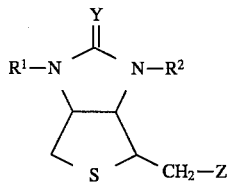

wherein $R^1$ and $R^2$ represent independently hydrogen, an alkyl group, a phenyl group which may be substituted, an acyl group, an alkenylmethyl group, or a benzyl group which may be substituted, Y represents an oxygen atom, or a sulfur atom, and Z represents an alkyl group having a carboxyl group or an alkoxy group at terminal, comprising catalytically reducing a compound having the general formula (1):

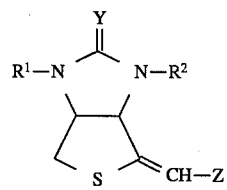

wherein $R^1$, $R^2$, Y, and Z are as defined above, with hydrogen in a solvent mixture of at least one of alcohols and water in the presence of a palladium catalyst soluble in organic solvents.

Furthermore, the present invention provides a process for producing a thiophene derivative expressed by the general formula (2) comprising catalytically reducing a compound having the general formula (1) with hydrogen in the presence of a palladium catalyst soluble in organic solvents in a solvent mixture of at least one of alcohols and water, and then adding a flocculant and a adsorbent to remove the flocculated palladium catalyst out of the system.

The present invention is described in detail under.

The compounds as represented by the general formula (1) to be used in the present invention may be either optically active substances or racemic substances.

Those compounds which correspond to thiophene derivatives expressed by the general formula (2) wherein $R^1$ and $R^2$ are a benzyl group, Y is an oxygen atom, and Z is —$CH_2CH_2CH_2COOH$, produced by the present invention can be converted to biotin by reacting them with methanesulfonic acid in accordance with the technique as disclosed in Japanese Patent KOKOKU (Post-Exam. Publication) No. Sho 63- 8954.

The compounds as expressed by the general formulas (1) and (2) of the present invention include those wherein $R^1$ and $R^2$ are an alkyl group having 1 to 10 carbon atoms. The substituents contained in the phenyl groups which may be substituted include $C_1$ to $C_6$ alkyl groups, $C_1$ to $C_6$ alkoxy groups and halogen atoms. The acyl groups include acetyl, propionyl, butyryl, and valeryl. The substituents contained in the benzyl groups which may be substituted include $C_1$ to $C_6$ alkyl groups, $C_1$ to $C_6$ alkoxy groups and halogen atoms. The alkenyl groups of the alkenylmethyl groups include those having 1 to 10 carbon atoms. In the alkyl groups having a carboxyl group or alkoxy group at terminal represented by Z, the alkoxy and alkyl groups include those having 1 to 10 carbon atoms.

The present invention employs a solvent mixture of at least one of alcohols and water. Particularly, the presence of water is important. If no water is present, a greater amount of the palladium catalyst is required. The alcohols are necessary for dissolving the compounds expressed by the general formula (1) as starting materials. If only water is used as solvent, the reaction system becomes non-homogeneous, and the proceeding of the reduction reaction is inhibited.

The alcohols to be used include methanol, ethanol, 2-propanol, and the like, and the use of 2-propanol is particularly preferred. The ratio of water to alcohols by weight (water/alcohols) is generally in the rage of 0.01 to 5, preferably 0.1 to 3. The amount of alcohol to be used is not critical.

The organosolvent-soluble palladium catalysts to be used as catalysts include, for example, palladium acetate, palladium propionate, dichlorobis(triphenylphosphine) palladium, di-μ-chlorobis(η-aryl) palladium, dichloro(η-1,5-cyclooctadiene) palladium, dichloro(η-2,5-norbornadiene) palladium, dichlorobis(acetonitrile) palladium, dichlorobis(benzonitrile) palladium, dichlorobis(N,N-dimethylformamide) palladium, bis(acetylacetonato) palladium, bis(dimethylglyoximato) palladium, and the like, and particularly the use of palladium acetate is preferred.

The amount of catalyst to be used is generally 0.05 mole percent or more, preferably 0.5 mole percent or more of the compound expressed by the general formula (1). The upper limit is not critical, but generally not higher than 1.5 mole percent from the economical standpoint.

The hydrogen pressure is generally in the range of 1 to 50 $kg/cm^2$, preferably 5 to 30 $kg/cm^2$.

The reaction temperature is generally in the range of 0° to 200° C., preferably 50° to 150° C.

The palladium catalysts after the reduction reaction may be flocculated, for example, by an appropriate means of altering the solvent system and removed out of the system by filtration.

For the removal of the palladium catalysts after the reaction in the present invention, one can use flocculants. Such flocculants include electrolytes, practically halides, nitrates and sulfates of metals such as aluminum, magnesium, sodium, potassium, and iron, or phase transfer catalysts such as benzyltriethylammonium chloride, tetra-n-butylammonium bromide and the like, preferably multi-valent electrolytes, more preferably aluminum sulfate. The term "multi-valent electrolytes" as used here refers to the electrolytes with at least one of cations or anions being multi-valent.

The amount of flocculant to be used is generally not lower than 1% by weight, preferably 10% by weight or more based on the weight of palladium catalyst. The upper limit is not critical, but generally not higher than 2000% by weight.

The adsorbents to be used in the present invention include, for example, activated carbon, activated clay, diatomaceous earth, silica gel, alumina and the like, and particularly the use of activated carbon is preferred. The amount of adsorbent to be used is generally not less than 10% by weight, preferably not less than 100% by weight based on the weight of palladium catalyst. The upper limit is not critical, but generally not higher than 5000%. The temperature for the catalyst flocculation is generally in the range of 0° to 100° C., preferably 30° to 70° C.

After the removal of catalyst, an ordinary post-treatment such as concentration may be performed to obtain a compound expressed by the general formula (2) at a high yield.

The present process enables advantageously the industrial production of a compound expressed by the general formula (2) useful for an intermediate for production of biotin.

DESCRIPTION OF THE PREFERRED EMBODIMENTS

The present invention will be further illustrated in detail under with reference to the following examples, without being limited thereto.

Example 1

132 grams of 5-[(3aS, 6aR)- 4,6-dibenzyl-5-oxohexahydro-1H-thieno[3,4-d] imidazol-1-ylidene] pentanoic acid were dissolved in a solution of 450 grams of 2-propanol and 200 grams of water, and catalytically reduced with one gram of palladium acetate (1.4 mole percent) under a hydrogen pressure of 20 kg/cm$^2$ at a temperature of 70° C. for three hours. After the reaction, 1000 grams of hexane and 20 grams of activated carbon were added to the reaction solution, and filtrated to remove the catalyst. The filtrate was condensed under a reduced pressure to yield 131 grams of 5-[(1R, 3aS, 6aR)- 4,6-dibenzyl-5-oxohexahydro-1H-thieno [3,4-d] imidazol-1-yl] pentanoic acid as an oily material. Purity: 98% (according to the LC-IS method. The same method was applied to the following.).

The compound was left to stand overnight in an refrigerator to be crystallized and recrystallized from 2-propanol and hexane. Mp. 91°–92° C.; Degree of optical rotation [α]$_D^{23}$: −26.8 (C=1.0, methanol); Purity; 99.3%.

Example 2

The same reaction and the same post-treatment were conducted as in Example 1, except that 1.72 grams (1.4 mole percent) of dichlorobis(benzonitrile) palladium were used instead of one gram of palladium acetate in Example 1, to yield 134 grams of 5-[(1R, 3aS, 6aR)- 4,6-dibenzyl-5-oxohexahydro-1H-thieno[3,4-d] imidazol-1-yl] pentanoic acid as an oily material. Purity: 96%.

Comparative Example 1

The same reaction and the same post-treatment were conducted as in Example 1, except that 0.63 gram (1.4 mole percent) of palladium oxide was used instead of one gram of palladium acetate in Example 1, to yield a mixture of 13.2 grams of 5-[(1R, 3aS, 6aR)- 4,6-dibenzyl-5-oxohexahydro-1H-thieno[3,4-d] imidazol-1-yl] pentanoic acid and 118 grams of the starting olefin as an oily material.

Example 3

The same reaction and the same post-treatment were performed as in Example 1, except that 450 grams of methanol were used instead of 450 grams of 2-propanol in Example 1, to yield 131 grams of 5-[(1R, 3aS, 6 aR)-4,6-dibenzyl-5-oxohexahydro-1H-thieno[ 3,4-d]imidazol-1-yl] pentanoic acid as an oily material. Purity: 98%.

Comparative Example 2

The same reaction and the same post-treatment were conducted as in Example 1, except that 650 grams of 2-propanol were used instead of 450 grams of 2-propanol and 200 grams of water in Example 1, to yield a mixture of 70 grams of 5-[(1R, 3aS, 6aR)- 4,6-dibenzyl-5-oxohexahydro-1H-thieno[3,4-d] imidazol-1-yl] pentanoic acid and 61 grams of the starting olefin as an oily material.

Example 4

127 grams of (3aS, 6aR)-4,6-dibenzyl- 1-(3-ethoxypropylidene)-5-oxohexahydro-1H-thieno[ 3,4-d]imidazole were dissolved in a solution of 220 grams of 2-propanol and 40 grams of water, and catalytically reduced with 0.38 gram of palladium acetate (0.55 mole percent) under a hydrogen pressure of 20 kg/cm$^2$ at a temperature of 60° C. for three hours. After the reaction, 500 grams of hexane and 10 grams of activated carbon were added to the reaction solution, and filtrated to remove the catalyst. The filtrate was condensed under a reduced pressure to yield 127 grams of (1R, 3aS, 6aR)-4,6-dibenzyl-1-( 3-ethoxypropyl)-5-oxohexahydro-1H-thieno[3,4-d] imidazole as an oily material. Purity: 97%.

Example 5

The same reaction and the same post-treatment were carried out as in Example 4, except that 0.65 gram (0.55 mole percent) of dichlorobis(benzonitrile) palladium were used instead of 0.38 gram of palladium acetate in Example 4, to yield 128 grams of (1R, 3aS, 6aR) - 4,6-dibenzyl-1-(3-ethoxypropyl)-5-oxohexahydro- 1H-thieno[3,4-d]imidazole as an oily material. Purity: 96%.

Comparative Example 3

The same reaction and the same post-treatment as in Example 4 were repeated, except that 0.24 gram (0.55 mole percent) of palladium oxide was used instead of 0.38 gram of palladium acetate in Example 4, to yield a mixture of 13.2 grams of (1R, 3aS, 6aR)-4,6-dibenzyl- 1-(3-ethoxypropyl)-5-oxohexahydro-1H-thieno[ 3,4-d]imidazole and 113 grams of the starting olefin as an oily material.

Example 6

The same reaction and the same post-treatment as in Example 4 were performed, except that 220 grams of methanol were used instead of 220 grams of 2-propanol in Example 4, to yield 128 grams of (1R, 3aS, 6aR)-4,6-dibenzyl-1-(3-ethoxypropyl)- 5-oxohexahydro-1H-thieno[3,4-d]imidazole as an oily material. Purity: 96%.

Comparative Example 4

The same reaction and the same post-treatment were conducted as in Example 4, except that 260 grams of 2-propanol were used instead of 220 grams of 2-propanol and 40 grams of water in Example 4, to yield a mixture of 65 grams of (1R, 3aS, 6aR) -4,6-dibenzyl-1-( 3-ethoxypropyl)-5-oxohexahydro-1H-thieno[3,4-d] imidazole and 62 grams of the starting (3aS, 6aR)-4,6-dibenzyl-1-( 3-ethoxypropylidene)-5-oxohexahydro-1H-thieno[ 3,4-d]imidazole as an oily material.

Example 7

132 grams of 5-[(3aS, 6aR)- 4,6-dibenzyl-5-oxohexahydro-1H-thieno[3,4-d] imidazol-1-ylidene] pentanoic acid were dissolved in a solution of 450 grams of 2-propanol and 200 grams of water, and catalytically reduced with one gram of palladium acetate (1.4 mole percent) under a hydrogen pressure of 20 kg/cm$^2$ at a temperature of 70 ° C. for three hours.

After the reaction, 0.1 gram of aluminum sulfate and 15 grams of activated carbon were added to the reaction solution and stirred at a temperature of 60° C. for two hours to flocculate the catalyst which was filtrated to be removed. The filtrate was condensed under a reduced pressure to yield 131 grams of 5-[(1R, 3aS, 6aR)-4,6-dibenzyl-5-oxohexahydro-1H-thieno[ 3,4-d]imidazol-1-yl] pentanoic acid as an oily material. Purity: 98%. The compound was left to stand overnight in a refrigerator to be crystallized and recrystallized from 2-propanol and hexane. Mp. 91°–92° C.; $[\alpha]_D^{23}$: – 26.8 (C=1.0, methanol); Purity: 99.3%.

Example 8

The same reaction and the same post-treatment as in Example 7 were conducted, except that 1.72 grams (1.4 mole percent) of dichlorobis(benzonitrile) palladium were used instead of one gram of palladium acetate in Example 7, to yield 134 grams of 5-[(1R, 3aS, 6 aR)-4,6-dibenzyl-5-oxohexahydro-1H-thieno[ 3,4-d]imidazol-1-yl] pentanoic acid as an oily material. Purity: 96%.

Example 9

The same reaction and the same post-treatment as in Example 7 were carried out, except that 450 grams of methanol were used instead of 450 grams of 2-propanol in Example 7, to yield 131 grams of 5-[(1R, 3aS, 6aR)-4,6-dibenzyl-5-oxohexahydro- 1H-thieno[3,4-d]imidazol-1-yl] pentanoic acid as an oily material. Purity: 98%.

Example 10

The same reaction and the same post-treatment as in Example 7 were carried out, except that 20 grams of potassium chloride were used instead of 0.1 gram of aluminum sulfate in Example 7, to yield 131 grams of 5-[( 1R, 3aS, 6aR)-4,6-dibenzyl-5-oxohexahydro-1H-thieno[ 3,4-d] imidazol-1-yl] pentanoic acid as an oily material.

Example 11

The same reaction and the same post-treatment as in Example 7 were repeated, except that 15 grams of activated clay were used instead of 15 grams of activated carbon in Example 7, to yield 131 grams of 5-[( 1R, 3aS, 6aR) -4,6-dibenzyl-5-oxohexahydro-1H-thieno[ 3,4-d]imidazol-1-yl] pentanoic acid as an oily material. Purity: 98%.

Example 12

127 grams of (3aS, 6aR)-4,6-dibenzyl- 1-(3-ethoxypropylidene)-5-oxohexahydro-1H-thieno[ 3,4-d]imidazole were dissolved in a solution of 220 grams of 2-propanol and 40 grams of water, and catalytically reduced with 0.38 gram of palladium acetate (0.55 mole percent) under a hydrogen pressure of 20 kg/cm$^2$ at a temperature of 60° C. for three hours.

After the reaction, 5.5 grams of aluminum sulfate and 4.5 grams of activated carbon were added to the reaction solution, and stirred at a temperature of 60° C. for two hours to flocculate the catalyst which was filtrated to be removed. The filtrate was condensed under a reduced pressure to yield 127 grams of (1R, 3aS, 6aR)-4,6-dibenzyl-1-(3-ethoxypropyl)- 5-oxohexahydro-1H-thieno[3,4-d]imidazole as an oily material. Purity: 97%.

Example 13

The same reaction and the same post-treatment were performed as in Example 12, except that 0.65 gram (0.55 mole percent) of dichlorobis(benzonitrile) palladium were used instead of 0.38 gram of palladium acetate in Example 12, to yield 128 grams of (1R, 3aS, 6aR)- 4,6-dibenzyl-1-(3-ethoxypropyl)-5-oxohexahydro- 1H-thieno[3,4-d]imidazole as an oily material. Purity: 96%.

Example 14

The same reaction and the same post-treatment as in Example 12 were repeated, except that 220 grams of methanol were used instead of 220 grams of 2-propanol in Example 12, to yield 127 grams of (1R, 3aS, 6aR) -4,6-dibenzyl-1-(3-ethoxypropyl)- 5-oxohexahydro-1H-thieno[3, 4-d]imidazole as an oily material. Purity: 97%.

What is claimed is:

1. A process for producing a thiophene derivative expressed by the general formula (2):

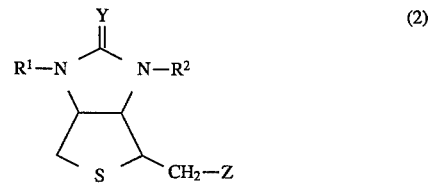

wherein $R^1$ and $R^2$ represent independently hydrogen, an alkyl group, a phenyl group, a substituted phenyl group, an acyl group, an alkenylmethyl group, a benzyl group, or a substituted benzyl group, Y represents an oxygen atom or a sulfur atom, and Z represents an alkyl group having a terminal carboxyl group or a terminal alkoxy group, comprising catalytically reducing a compound having the general formula (1):

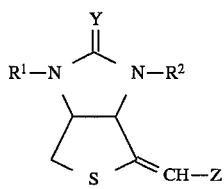

wherein $R^1$, $R^2$, Y, and Z are as defined above, with hydrogen in a solvent mixture of at least one alcohol and water using a palladium catalyst soluble in organic solvents, wherein the palladium catalyst is one selected from the group consisting of palladium acetate, palladium propionate, dichlorobis (triphenylphosphine) palladium, di-μ-chlorobis (η-aryl) palladium, dichloro (η-1,5-cyclooctadiene) palladium, dichlorobis (η-2,5-norbornadiene) palladium, dichlorobis (acetonitrile) palladium, dichlorobis (benzonitrile) palladium, dichlorobis (N,N-dimethylformamide) palladium, bis (acetylacetonato) palladium and bis (dimethyl-glyoximato) palladium.

2. A process for producing a thiophene derivate represented by the general formula (2):

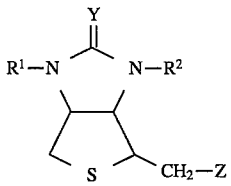

wherein $R^1$ and $R^2$ represent independently hydrogen, an alkyl group, a phenyl group, a substituted phenyl group, an acyl group, an alkenylmethyl group, a benzyl group, or a substituted benzyl group, Y represents an oxygen atom or a sulfur atom, and Z represents an alkyl group having a terminal carboxyl group or a terminal alkoxy group, comprising catalytically reducing a compound having the general formula (1):

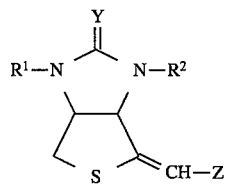

wherein $R^1$, $R^2$, Y and Z are as defined above, with hydrogen in a solvent mixture of at least one alcohol and water using a palladium catalyst dispersed in said solvent mixture, wherein the palladium catalyst is one selected from the group consisting of palladium acetate, palladium propionate, dichlorobis (triphenylphosphine) palladium, di-μ-chlorobis (η-aryl) palladium, dichloro (η-1,5-cyclooctadiene) palladium, dichlorobis (η-2,5-norbornadiene) palladium, dichlorobis (acetonitrile) palladium, dichlorobis (benzonitrile) palladium, dichlorobis (N,N-dimethylformamide) palladium, bis (acetylacetonato) palladium and bis (dimethyl-glyoximato) palladium, and then adding a flocculent and adsorbent to flocculate the palladium which is removed out of the system.

3. The process according to claim 1 or claim 2, wherein $R^1$ and $R^2$ are a benzyl group, Y is an oxygen atom, and Z is a 3-carboxypropyl group.

4. The process according to claim 1 or claim 2, wherein $R^1$ and $R^2$ are a benzyl group, Y is an oxygen atom, and Z is a 2-ethoxyethyl group.

5. The process according to claim 1 or claim 2, wherein the amount of said palladium catalyst is in the range of 0.05 to 1.5 mole percent of the compound expressed by the general formula (1).

6. The process according to claim 1 or claim 2, wherein the amount of said palladium catalyst is in the range of 0.5 to 1.5 mole percent of the compound expressed by the general formula (1).

7. The process according to claim 1 or claim 2, wherein said alcohol is 2-propanol.

8. The process according to claim 1 or claim 2, wherein said alcohol is methanol.

9. The process according to claim 1 or claim 2, wherein the ratio of water to alcohol (water/alcohol) by weight is from 0.01 to 5.

10. The process according to claim 1 or claim 2, wherein the ratio of water to alcohol (water/alcohol) by weight is from 0.1 to 3.

11. The process according to claim 1, or claim 2, wherein said catalytic reduction reaction is performed under a hydrogen pressure of 1 to 50 kg/cm².

12. The process according to claim 1 or claim 2, wherein said catalytic reduction reaction is performed under a hydrogen pressure of 5 to 30 kg/cm².

13. The process according to claim 1 or claim 2, wherein the reaction temperature is in the range of 0° to 200° C.

14. The process according to claim 1 or claim 2, wherein the reaction temperature is in the range of 50° to 150° C.

15. The process according to claim 2, wherein said flocculant is a multi-valent electrolyte.

16. The process according to claim 2, wherein said adsorbent is activated carbon.

17. The process according to claim 2, wherein said flocculant is a multi-valent electrolyte and said adsorbent is activated carbon.

18. The process according to claim 1 or claim 2, which further comprises adding the palladium catalyst to the compound represented by the formula (1) in the solvent mixture prior to the catalytic reduction.

19. The process according to claim 1, wherein said palladium catalyst is palladium acetate.

20. The process according to claim 1, wherein said palladium catalyst is dichlorobis (benzonitrile) palladium.

21. The process according to claim 2, wherein said palladium catalyst is palladium acetate.

22. The process according to claim 2, wherein said palladium catalyst is dichlorobis (benzonitrile) palladium.

23. A process for producing a thiophene derivative expressed by the general formula (2):

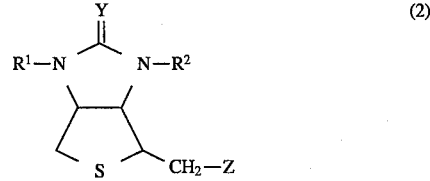

wherein $R^1$ and $R^2$ represent independently hydrogen, an alkyl group, a phenyl group, a substituted phenyl group, an acyl group, an alkenylmethyl group, a benzyl group, or a substituted benzyl group, Y represents an oxygen atom or a sulfur atom, and Z represents an alkyl group having a terminal carboxyl group or a terminal alkoxy group, comprising catalytically reducing a compound having the general formula (1):

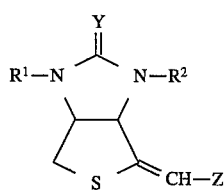

wherein $R^1$, $R^2$, Y, and Z are as defined above, with hydrogen in a solvent mixture of at least one alcohol and water using a palladium carboxylate catalyst soluble in organic solvents, wherein the palladium carboxylate catalyst is palladium acetate or palladium propionate.

24. A process for producing a thiophene derivate represented by the general formula (2):

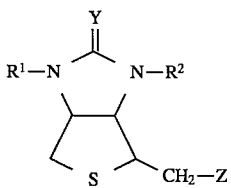

wherein $R^1$ and $R^2$ represent independently hydrogen, an alkyl group, a phenyl group, a substituted phenyl group, an acyl group, an alkenylmethyl group, a benzyl group, or a substituted benzyl group, Y represents an oxygen atom or a sulfur atom, and Z represents an alkyl group having a terminal carboxyl group or a terminal alkoxy group, comprising catalytically reducing a compound having the general formula (1):

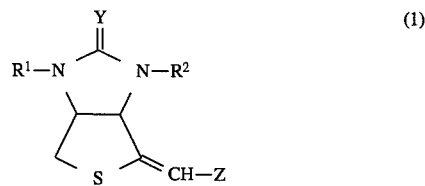

wherein $R^1$, $R^2$, Y and Z are as defined above, with hydrogen in a solvent mixture of at least one alcohol and water using a palladium catalyst dispersed in said solvent mixture, wherein the palladium catalyst is a palladium carboxylate which is palladium acetate or palladium propionate, and then adding a flocculent and adsorbent to flocculate the palladium which is removed out of the system.

* * * * *